US00PP26755P2

(12) United States Plant Patent
Lichacz

(10) Patent No.: US PP26,755 P2
(45) Date of Patent: May 24, 2016

(54) ***HOSTA* PLANT NAMED 'AFTERGLOW'**

(50) Latin Name: ***Hosta* hybrid (Tratt.)**
Varietal Denomination: Afterglow

(71) Applicant: Susan Lichacz, Zeeland, MI (US)

(72) Inventor: Susan Lichacz, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 200 days.

(21) Appl. No.: 13/986,080

(22) Filed: Mar. 29, 2013

(51) Int. Cl.
*A01H 5/12* (2006.01)

(52) U.S. Cl.
USPC ..... Plt./353

(58) Field of Classification Search
USPC ..... Plt./353
See application file for complete search history.

(56) References Cited

PUBLICATIONS

Walters Gardens, Inc. Proven Winners Wholesale Catalog Summer 2012-Spring 2013 pp. 1-23.*

* cited by examiner

*Primary Examiner* — June Hwu

(57) ABSTRACT

A new and distinct *Hosta* plant named 'Afterglow' characterized by upright mounded habit, heart-shaped leaves with broad yellow margins and green leaf centers and light lavender buds opening to pale lavender flowers beginning in late June on arching scapes.

1 Drawing Sheet

Botanical classification: *Hosta* hybrid (Tratt.).
Variety denomination: 'Afterglow'.

BACKGROUND AND ORIGIN OF THE PLANT

The present invention relates to a new and distinct *hosta* plant, *Hosta* 'Afterglow' hereinafter also referred to as the new plant or just the cultivar name, 'Afterglow'. *Hosta* 'Afterglow' was discovered by Susan Lichacz in the summer of 2009 at a perennial plant nursery in Zeeland, Mich. *Hosta* 'Afterglow' is an uninduced whole plant mutation of *Hosta* 'Climax' discovered in a batch of tissue-culture propagated *Hosta* 'Climax' (not patented). The new plant has been asexually propagated by division at the same nursery in Zeeland, Mich. and also by careful tissue culture propagation since August of 2011 with the resultant asexually propagated plants having retained all the same traits as the original plant. *Hosta* 'Afterglow' is stable and reproduces true to type in successive generations of asexual reproduction.

There are almost 5,000 *hostas* registered with The American Hosta Society, which is the International Cultivar Registration Authority for the genus *Hosta*. The most similar *hosta* cultivars known to the applicant are: *Hosta* 'Academy Blushing Recluse' (not patented), 'Afternoon Delight' (not patented), 'Erie Magic' (not patented), 'El Capitan' (not patented), 'Goodness Gracious' U.S. Plant Pat. No. 23,081 and the original mutation parent *Hosta* 'Climax'. All of the above have a yellowish leaf margin with green to dark green leaf centers. 'Afterglow' is less rugose with a more rounded leaf than 'Academy Blushing Recluse'. The new plant has a less pointed leaf apex and is larger in leaf and habit than 'El Capitan' and more rounded in habit with less pointed in leaf apex than 'Erie Magic'. Compared to 'Afternoon Delight' the new plant has wider yellow variegation of the margins, and in comparison to 'Goodness Gracious' the new plant has a more rounded leaf, with deeper impressed adaxial veins and less acute apex. In comparison to 'Climax', the new plant has a wider yellow variegation of the margin.

The new plant, *Hosta* 'Afterglow' is different from all other *hosta* cultivars known to the inventor through the following combined characteristics:

1. Upright mounded habit.
2. Heart-shaped leaves with broad yellow margins and green leaf center.
3. Light lavender buds opening to pale lavender flowers beginning in late June on arching scapes.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
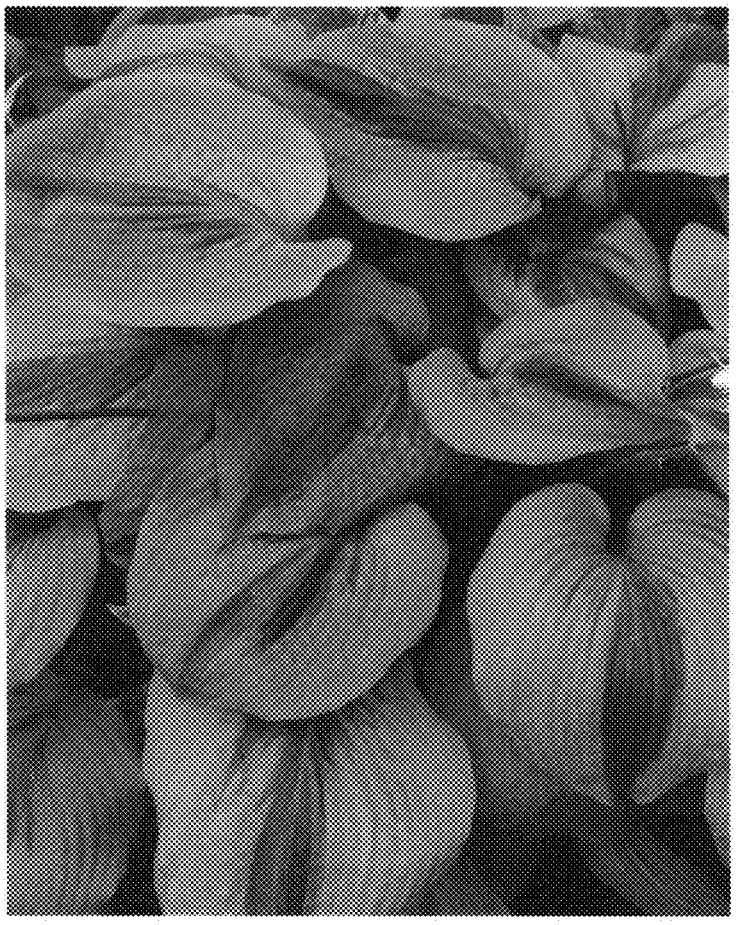
FIG. 1 shows the foliage of a three-year old plant in mid-season in Zeeland, Mich.
Figure 2:
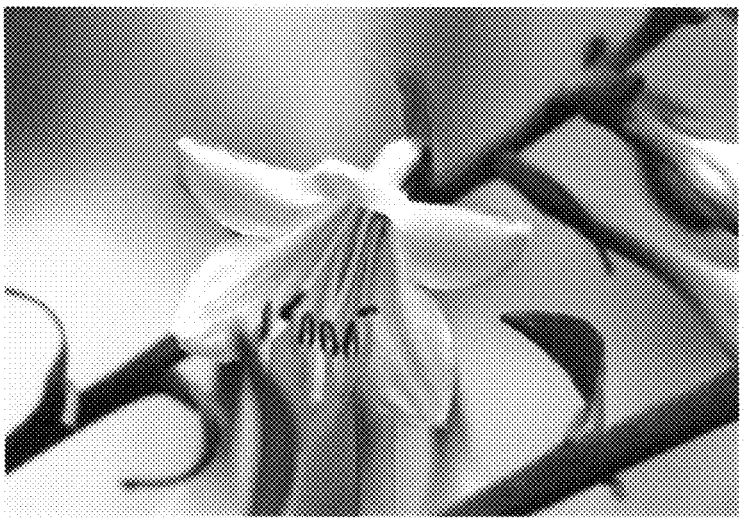
FIG. 2 shows a close-up of a flower on scape.

The following descriptions and color references are based on the 2001 edition of The Royal Horticultural Society Colour Chart except where common dictionary terms are used. The new plant, *Hosta* 'Afterglow', has not been observed under all possible environments. The phenotype may vary slightly with different environmental conditions, such as temperature, light, fertility, moisture and maturity levels, but without any change in the genotype. The following observations and size descriptions are of a potted three-year old plant in a shaded greenhouse in Zeeland, Mich. with and supplemental water and fertilizer.

Botanical classification: *Hosta*×hybrid.

Parentage: Whole plant mutation of *Hosta* 'Climax'.

Propagation: Garden division and sterile plant tissue culture.

Time to initiate roots from tissue culture: About two to three weeks.

Growth rate: Rapid.

Crop time: About 9 to 10 weeks to finish during the summer in a one-liter container from rooted tissue culture plantlet.

Rooting habit: Fleshy, lightly branching.

Plant shape and habit: Hardy herbaceous perennial with basal rosette of leaves emerging from rhizomes producing a symmetrical mound of broadly horizontal leaves.

Plant size: Foliage height about 52.0 cm tall from soil line to the top of the leaves and about 95.0 cm wide at the widest point just above soil line.

Foliage description: Entire, glabrous, adaxial blade dull with slightly glaucous, abaxial with glaucous bloom, cordate to nearly rounded, moderately rugose, broadly acute leaf apex with cordate base; blades flat to curving downward toward apex; 25 to 32 cm long and 17.5 to 21.0 cm wide, average 29 cm long and 19.0 cm wide; variegated with a green center and yellow margin width of 5.0 to 9.0 cm.

Bracts surrounding emerging shoot: Elliptic to ovate, with acute apex and truncate base below ground; smaller outer bracts becoming papery and drying by about mid-season; inner bracts sometimes persistent, adpressed to expanding shoots in early spring; leaves and petioles partially clasping and surrounding shoots, petioles and expanding leaves; varying in size with more inner bracts larger becoming more leaf-like; with largest about 8 cm long and 2 cm wide and smallest about 3 cm long and 1 cm wide; coloration with variegation identical to that of leaves.

Leaf blades: Simple, entire, bi-laterally symmetrical; glabrous and dull matte surface on top, glabrous and glaucous below; variegation pattern characteristically variable with the margin between 0.5 cm to 7.5 cm wide, generally wider with more maturity and wider at that apex and narrower at the center and base, with some long jetting of margin or center color into the edge or center and intermediate colors between the leaf center and margin more pronounced at the apical one third of leaf.

Leaf blade color: Early season shortly after emergence adaxial (top) center color between RHS 137B and RHS 137A; early season adaxial margin nearest RHS 152B; early season abaxial (underside) center between RHS N138C and RHS 138B; early season abaxial margin nearest RHS 146D; Mid-season and later summer adaxial centers nearest RHS 137C; mid-season and later adaxial margins nearest RHS 153C; mid-season and later abaxial center nearest RHS N138C; mid-season and later abaxial margins nearest RHS 151A; major intermediate colors where adaxial margin and center unevenly and irregularly fold over each other of lighter than RHS 137D, nearest RHS N144D, nearest RHS 138D and nearest RHS N144D; major intermediate colors where abaxial margin and center unevenly and irregularly fold over each other of nearest RHS 139D, nearest RHS 145A and nearest RHS 146D.

Petiole: Entire, glabrous concavo-convex; slightly arching from base of plant to leaf base, stiff; 18 to 27 cm long and 10 to 14 mm wide at base, average about 25 cm long and 12 mm wide.

Petiole color: Adaxial centers nearest RHS 137D; adaxial margins nearest RHS N144A; abaxial center nearest RHS 137D; abaxial margins nearest RHS 146D.

Veins: Parallel, impressed on adaxial side and raised on abaxial side, normally 14 to 16 pairs, increasing with maturity to a maximum at about 7 to 9-years old.

Veins color: Adaxial and abaxial veins the same color as the surrounding tissue.

Flower description:

*Buds two to three days prior to opening.*—Globose apex about 1.5 cm in diameter with base narrowing at about mid-length to about 0.4 cm diameter; about 5.5 cm long; distal buds smaller; Bud color: light lavender lighter than RHS 76D.

*Flowers.*—Perfect; funnelform; opening to 4.5 to 5.0 cm wide and 5.0 to 5.5 cm long, (distal flowers smaller), persists for a normal period, usually one day on plant or as cut flower; scapes remain effective with flowers from late June with 30 to 40 flowers per scape; no detectable fragrance.

Tepal: Two sets of three, glabrous, entire; fused at base; clavate with acute apex; each approximately 5.5 cm long and the inner set 1.5 cm wide and outer set 1.3 cm wide.

Tepal color: Coloring of both sets identical, inner surface center light lavender between RHS 85C and RHS 85D with inner margin white, lighter than RHS 155D or RHS N155D; outer surface near white, lighter than RHS 155D or RHS N155D in distal two thirds with a tepal base nearest RHS 85D.

Tepal veins: Three to five main veins, distinguishable by being impressed on abaxial surface and slightly darker in center than the surrounding tissue on adaxial surface to nearest RHS 85C.

Gynoecium:

*Style.*—Single, approximately 6.0 cm long, 1 mm diameter, curled upward sharply to about 90 degrees in the distal 1.2 cm; color lighter than RHS 155D.

*Stigma.*—Globose, about 2 mm in diameter, between RHS 155D and RHS 157D.

*Ovary.*—Oblong, about 0.9 cm long and 3.0 mm wide; color nearest RHS 146C.

Androecium: Filaments: six, approximately 4.8 cm long and less than 1 mm in diameter; curved upward to nearly 90 degrees in the apical 0.8 cm; color lighter than RHS 145D.

*Anthers.*—About 4.0 mm long, 1.5 mm wide, dorsifixed, dehiscent longitudinally; color between RHS N187B and RHS N187A.

*Pollen.*—Elliptic, less than 0.1 mm long, color closest to RHS 17B.

Peduncle: Usually one per mature division; glaucous, glabrous, round in cross-section; arching with maturity; up to about 95 cm tall, and up to 7.0 mm in diameter at base, average about 85 cm tall and 6.0 mm at base; average flowering portion of peduncle about 30 cm long; color between RHS 138A and RHS 138B.

Pedicel: Approximately 15.0 mm long, 2.0 mm wide; color distally nearest RHS 138D with tinting of RHS 84D and proximally between RHS 138B and RHS 138C.

Scape bracts: Sessile, entire, glabrous, slightly glaucous, dehiscent, lanceolate; single bract subtending individual or occasionally groups of up to four flowers; narrowly acute apex and truncate base; decreasing in size distally with one or two below first flowers; proximal bracts starting about 5.0 cm long and 10.0 mm wide at base, distal bracts about 1.6 cm long and 6.0 mm wide; proximal bracts curved downward back toward peduncle and distal bracts remain horizontal and concaved supporting flower.

Scape bract color: Nearest RHS 148C on both adaxial and abaxial surfaces.

Fruit: Tri-loculicidal capsule, about 3.8 cm long and 7.0 mm diameter; between color nearest RHS 146B shortly after pollination and lighter than RHS N199D near maturity.

Seed: Flattened single-winged nutlet with swollen embryo at one end; about 8 mm long, 3 mm wide and 1.5 mm thick at embryo; nearest RHS 202A.

Disease and pest resistance: The new plant has not shown any resistance to pests and diseases common to *hostas*. The plant grows best and shows best coloration with plenty of moisture, adequate drainage and light shade, but is able to tolerate some drought when mature and limited direct sun without leaf burn when provided sufficient water. Hardiness at least from USDA zone 3 through 9, and other disease resistance is typical of that of other *hostas*.

I claim:

1. A new and distinct ornamental *Hosta* plant cultivar named *Hosta* 'Afterglow' essentially as herein described and illustrated, with upright mounded habit, heart-shaped leaves with broad yellow margins and green leaf centers and light lavender buds opening to pale lavender flowers beginning in late June on arching scapes, suitable as a potted plant, for landscaping the garden, and for cut flower or cut foliage arrangements.

* * * * *